US006380277B1

(12) United States Patent
Oestreich et al.

(10) Patent No.: US 6,380,277 B1
(45) Date of Patent: Apr. 30, 2002

(54) IODONIUM SALT PHOTOINITIATORS CONTAINING URETHANE GROUPS FOR CATIONIC CURING

(75) Inventors: Sascha Oestreich; Andreas Weier; Stefanie Volkmer, all of Essen (DE)

(73) Assignee: Goldschmidt AG, Essen (DE)

( * ) Notice: Subject to any disclaimer, the term of this patent is extended or adjusted under 35 U.S.C. 154(b) by 0 days.

(21) Appl. No.: 09/665,525

(22) Filed: Sep. 19, 2000

(30) Foreign Application Priority Data

Sep. 21, 1999 (DE) .......................... 199 45 251

(51) Int. Cl.[7] .............................. C08F 2/50; C08J 3/28; C07C 271/12; C07C 271/44; C07C 271/46; C07C 269/02

(52) U.S. Cl. ..................... 522/31; 522/99; 522/148; 522/170; 522/181; 522/184; 522/188; 549/207; 556/64; 556/420; 568/13; 568/16; 568/18; 568/38; 568/74; 568/75; 568/583; 570/123; 570/127

(58) Field of Search ................ 568/8, 16, 13, 568/18, 38, 74, 75, 583; 522/31, 25, 15, 99, 148, 170, 181; 556/64, 420; 549/207; 570/123, 127

(56) References Cited

U.S. PATENT DOCUMENTS

| 4,279,717 A | 7/1981 | Eckberg et al. |
| 4,310,469 A | 1/1982 | Crivello |
| 4,374,066 A | 2/1983 | Crivello et al. |
| 5,057,549 A | 10/1991 | Herzig et al. |
| 5,073,643 A | 12/1991 | Crivello |
| 5,101,053 A | * 3/1992 | Boettcher |

FOREIGN PATENT DOCUMENTS

| DE | 25 18 639 A1 | 11/1975 |
| DE | 40 02 922 A1 | 8/1991 |
| EP | 0 334 056 A2 | 9/1989 |
| EP | 0 618 919 B1 | 10/1994 |
| EP | 1088813 | * 4/2001 |
| JP | 2001-139539 | * 5/2001 |

OTHER PUBLICATIONS

Kunze, et al., "Triplet Quenching by Onium Salts in Polar and Nonpolar Solvents", Journal of Photochemistry and Photobiology A; Chemistry 110 (1997) p. 115–122.

* cited by examiner

*Primary Examiner*—Susan W. Berman
(74) *Attorney, Agent, or Firm*—Frommer Lawrence & Haug LLP

(57) ABSTRACT

The present invention relates to iodonium salts containing urethane groups of reduced crystallization tendency, to a process for their preparation, and to their use for the radiation curing of cationically curing compositions.

22 Claims, No Drawings

IODONIUM SALT PHOTOINITIATORS CONTAINING URETHANE GROUPS FOR CATIONIC CURING

BACKGROUND OF THE INVENTION

1. Field of the Invention

The present invention relates to iodonium salts of reduced crystallization tendency containing urethane groups, to a process for their preparation, and to their use for the radiation curing of cationically curing compositions.

2. Description of the Related Art

Cationic photopolymerization is a rapid, efficient and environment-friendly means of curing cationically polymerizable monomers. Particularly efficient photoinitiators are diaryliodonium salts (I) and triarylsulfonium salts (II).

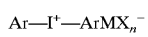 (I)

 (II)

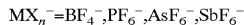

Diaryliodonium salts (I) in particular are known from the patent literature (DE-A-25 18 639, U.S. Pat. No. 4,279,717, EP-A-0 334 056, EP-B-0 618 919) and are used as photoinitiators for polymerizing cationically polymerizable substances. The cationically polymerizable substances, however, have little or no polarity, especially if the polymerizable groups are present in organopolysiloxanes. When adding these photoinitiators, therefore, it is a very common observation that, depending on the structure of the formulation, the miscibility and solubility of the photoinitiators is limited. For this reason, the aryl radicals of such onium salts are often substituted with alkyl chains in order to increase the solubility in organopolysiloxanes (U.S. Pat. No. 4,310,469 and U.S. Pat. No. 4,374,066).

In the case of hydroxyl-bearing iodonium salts as described in U.S. Pat. No. 5,073,643, the poor solubility in nonpolar media is attributed to the high crystallization tendency. The particular complexation characteristics of the hydroxyl-bearing iodonium salts of the general formula (III) result in a strong crystallization tendency of the compounds (A. Kunze, U. Müller, K. Tittes, J. P. Fouassier, F. Morlet-Savary, J. Photochemistry and Photobiology A: Chemistry, 110, 115–122 (1997)):

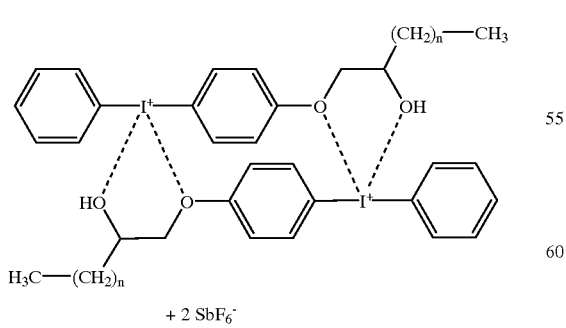 (III)

The two oxygen atoms in the molecule act as ligands for a second iodonium ion. This aggregation behavior promotes the formation of crystals.

In the preparation of these salts, the strong crystallization tendency is entirely desirable, since it means that the compounds can be recovered as powders in a high purity by simple recrystallization. In this way, they are easy and cost effective to prepare. Such iodonium salts are commercially available, for example, under the name CD-1012 from Sartomer.

The high crystallization tendency has an adverse effect, however, if the iodonium salts are to be dissolved in nonpolar media, such as organopolysiloxanes. In this case either they are insoluble or a solid precipitate forms after just a short time.

Because of their inhomogeneity, such coatings cure poorly on UV irradiation. However, it is also possible that, as a result of the inhomogeneity, massive surface defects (craters, wrinkles, specks, etc.) appear even during the application of a thin coat on a substrate.

OBJECTS OF THE INVENTION

It is an object of the present invention to modify hydroxyl-bearing iodonium salts in a particularly cost-effective and simple manner such that the crystallization tendency is greatly reduced and good compatibility, especially with organopolysiloxanes containing epoxy groups, is established, and the resulting compounds are stable to hydrolysis, so that reformation of hydroxyl-bearing iodonium salts in the course of storage is impossible.

SUMMARY OF THE INVENTION

These objects are achieved by means of iodonium salts of the general formula (IV)

 (IV)

where

I is iodine, $X^-$ is an anion of a complex metal salt and/or of a strong acid, $R^1$ is the radical

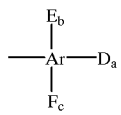

in which

Ar is an aromatic hydrocarbon radical, preferably, having 6 to 14 carbon atoms per radical or is an aromatic hydrocarbon radical containing at least one oxygen and/or sulfur atom and, preferably, having 5 to 15 ring atoms per radical, a is 1, 2 or 3, b is 0, 1 or 2, c is 0, 1 or 2, D, E and F are each substituents of Ar, D being a radical of the formula

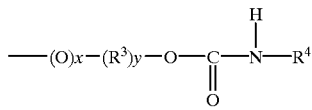

where
x is 0 or 1,
y is 0 or 1,
R³ is a linear or branched divalent hydrocarbon radical, preferably, having 1 to 40 carbon atoms per radical, which can be interrupted, if desired, by at least one oxygen atom and/or at least one sulfur atom and/or at least one carboxyl group, R⁴ is a monovalent linear, branched and/or cyclic alkyl, aryl, haloalkyl and/or haloaryl radical, preferably, having 1 to 40 carbon atoms, which can be interrupted, if desired, by at least one oxygen atom and/or at least one sulfur atom and/or at least one urethane group and/or ester group, and which can, if desired, contain hydrophobicizing substituents and/or at least one isocyanate group,
E is a radical of the formula

F is a radical of the formula

R² is a radical of the formula

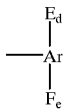

where
R⁵ is a monovalent hydrocarbon radical, preferably having 1 to 18 carbon atoms per radical, which can be interrupted, if desired, by at least one oxygen atom,
R⁶ is a monovalent hydrocarbon radical, preferably, having 1 to 18 carbon atoms per radical, which can be interrupted, if desired, by at least one oxygen atom,
d is 0, 1 or 2, and
e is 0, 1 or 2.

Surprisingly it has been found that the formation of a urethane from hydroxyl-containing iodonium salts makes it possible to reduce considerably the crystallization tendency, to improve substantially the compatibility with organopolysiloxanes containing epoxy groups, and to increase considerably the hydrolytic stability relative to iodonium salts containing Si—O—C bonds (see German Patent Application 19901531.7).

DESCRIPTION OF PREFERRED EMBODIMENTS

Preferred examples of aromatic hydrocarbon radicals Ar are the phenyl, naphthyl and anthryl radicals.

Preferred examples of aromatic hydrocarbon radicals Ar containing at least one oxygen and/or sulfur atom are the 2-furyl, 3-furyl, 2-thienyl and 3-thienyl radicals.

Preferred examples of the divalent hydrocarbon radical R³ which can be interrupted by at least one oxygen atom and/or at least one sulfur atom and/or a carboxyl group are —CH₂—, —CH₂—CH₂—, —CH₂—CH₂—O—CH₂—CH₂—, —CH₂—CH(CH₃)—, —CH₂—CH(CH₂CH₃)—, —CH₂—CH((CH₂)₃CH₃)—, —CH₂—CH((CH₂)₁₁CH₃)—,

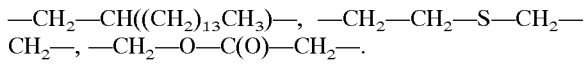

—CH₂—CH((CH₂)₁₃CH₃)—, —CH₂—CH₂—S—CH₂—CH₂—, —CH₂—O—C(O)—CH₂—.

Preferred examples of R⁴, the monovalent linear, branched and/or cyclic alkyl, aryl, haloalkyl and/or haloaryl radical having 1 to 40 carbon atoms, which can be interrupted, if desired, by at least one oxygen atom and/or at least one sulfur atom and/or at least one urethane group and/or ester group, and which can, if desired, contain hydrophobicizing substituents and/or at least one isocyanate group, are alkyl radicals, such as the methyl, ethyl, n-propyl, isopropyl, n-butyl, isobutyl, tert-butyl, n-pentyl, isopentyl, neopentyl, and tert-pentyl radical; hexyl radicals, such as the n-hexyl radical, for example, the cyclohexyl radical; heptyl radicals, such as the n-heptyl radical; octyl radicals, such as the n-octyl radical and isooctyl radicals, such as the 2,2,4-trimethylpentyl radical; nonyl radicals, such as the n-nonyl radical; decyl radicals, such as the n-decyl radical; dodecyl radicals, such as the n-dodecyl radical, and octadecyl radicals, such as the n-octadecyl radical; aryl radicals, such as the phenyl, naphthyl and anthryl radical; haloalkyl radicals, such as the chloromethyl, trichloromethyl, trifluoromethyl, pentafluoroethyl and heptafluoropropyl radical; haloaryl radicals, such as the bromophenyl, chlorophenyl, fluorophenyl, difluorophenyl, fluoro(trifluoromethyl)phenyl, pentafluorophenyl, (trifluoromethyl)phenyl, (trifluoromethylthio)phenyl and trifluoromethoxyphenyl radical.

The abovementioned examples of the radical R⁴ also apply in their entirety to the radicals R⁵ and R⁶.

Examples of hydrocarbons R⁴, R⁵ and R⁶ interrupted by at least one oxygen atom and/or sulfur atom are —CH₂—CH₂—O—CH₃, —CH₂—CH₂O—CH₂CH₃ and —CH₂—CH₂—S—CH₂CH₃.

Examples of the radical R⁴ interrupted by at least one urethane group and/or ester group, and being able to contain, if desired, hydrophobicizing substituents and/or at least one isocyanate group, are

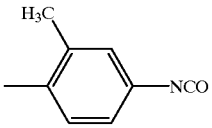

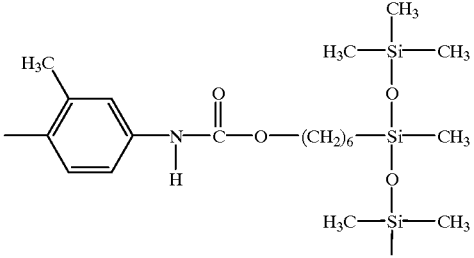

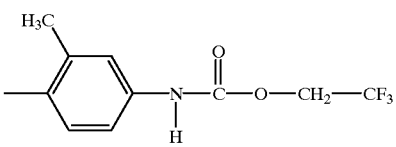

Preferred examples of radicals D are
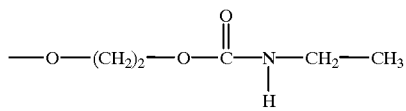
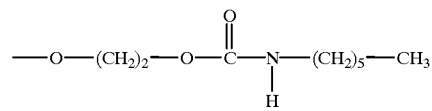
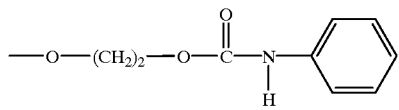
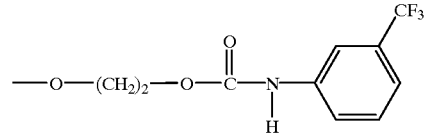
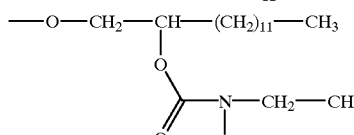
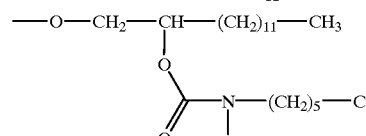
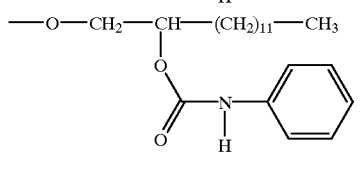
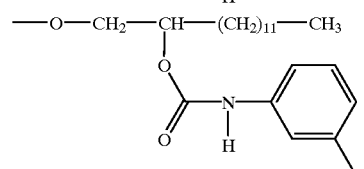
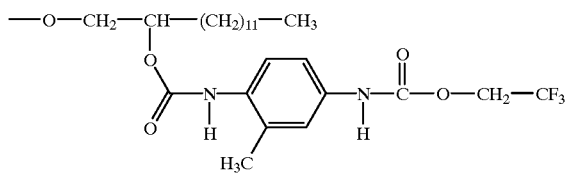
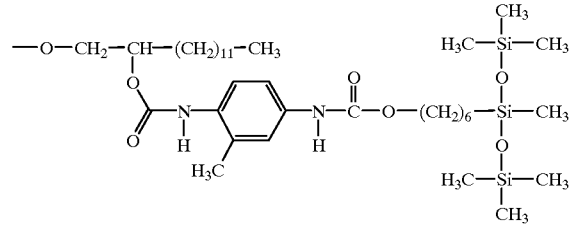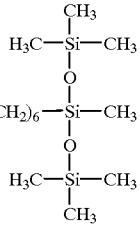
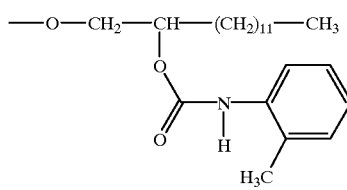
Preferred examples of radicals E are the methoxy, ethoxy and n-butoxy radical.
Preferred examples of radicals F are methyl, ethyl, propyl, 2-methylpropyl and the n-butyl radical.
Preferred examples of radicals $R^1$ are
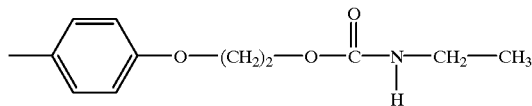
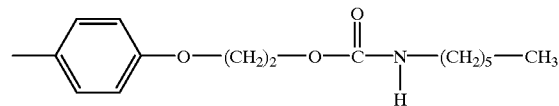
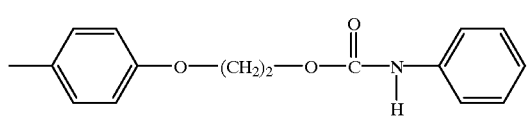
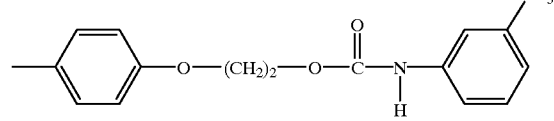

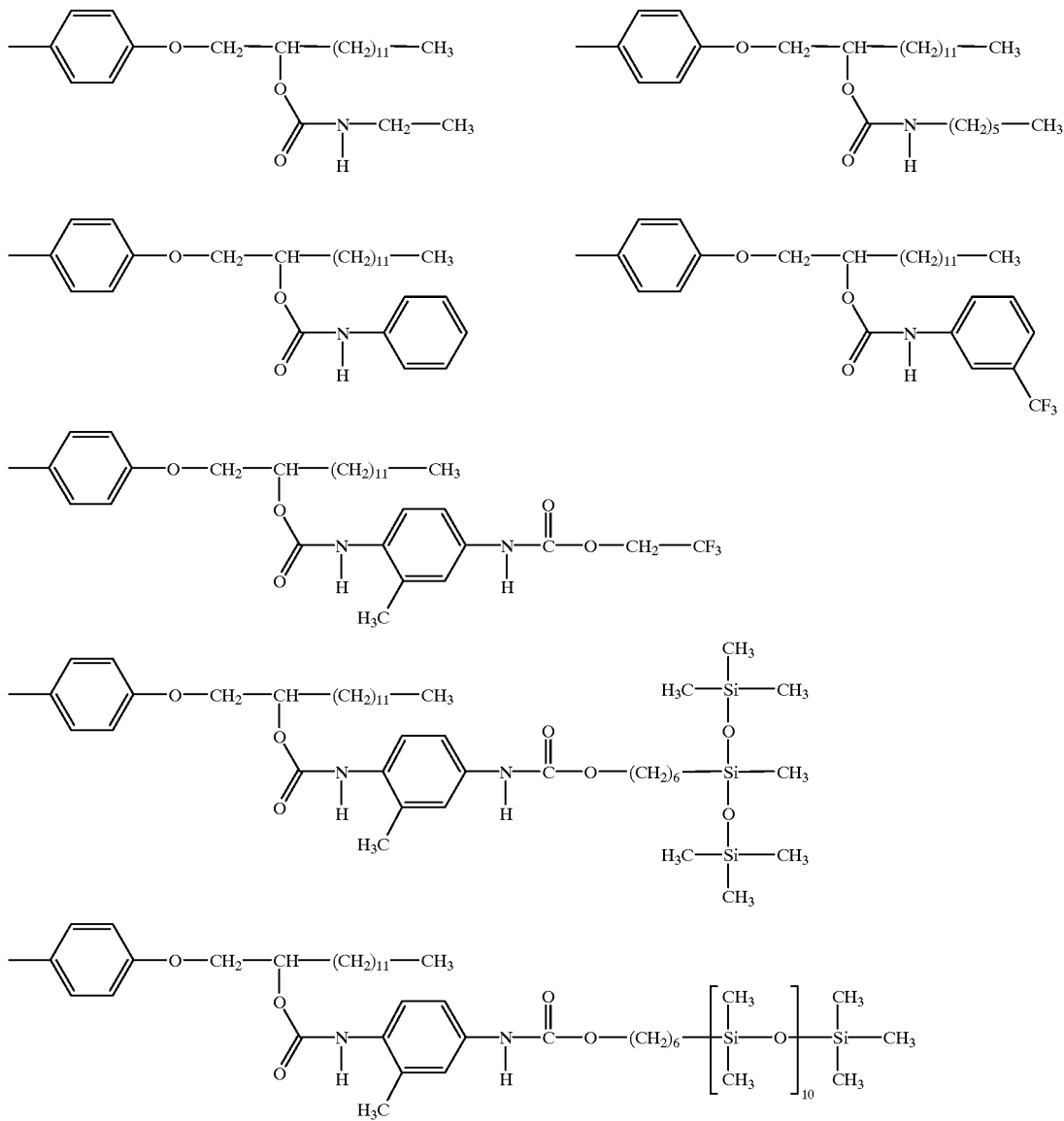

Preferred examples of radicals R² are the phenyl, 4-methylphenyl, 3-methoxyphenyl and 4-methoxyphenyl radical.

Preferred examples of anions X⁻ of a complex metal salt and/or of a strong acid are tosylate, $SbF_6^-$, $PF_6^-$, $BF_4^-$, $F_3CSO_3^-$, $F_3CCO_2^-$, $AsF_6^-$, $ClO_4^-$, $HSO_4^-$. For the purposes of the present invention, strong acids embrace, in particular, strong Brönsted acids.

Preferred iodonium salts of reduced crystallization tendency are those of the general formula (V)

where D and X⁻ are as defined previously.

Particularly preferred iodonium salts of reduced crystallization tendency are those of the formula (VI)

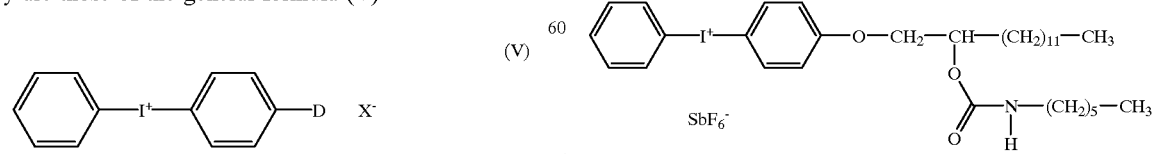

and of the formula (VII)

$$\text{(VII)}$$

[Structure: phenyl-I⁺-C₆H₄-O-CH₂-CH(O-C(=O)-NH-C₆H₄-CF₃)-(CH₂)₁₁-CH₃, SbF₆⁻]

The crystallization tendency of the iodonium salts modified in this way is substantially reduced in relation to the abovementioned prior art. For example, at room temperature the iodonium salt (VII) is a viscous liquid, whereas the comparable hydroxyl-containing iodonium salt having the formula (VIII) below $$\text{(VIII)}$$

[Structure: phenyl-I⁺-C₆H₄-O-CH₂-CH(OH)-(CH₂)₁₁-CH₃, SbF₆⁻]

is a powder having a melting point of 91° C., which is available under the trade name CD-1012 from Sartomer.

Likewise, the solubility of the iodonium salts of the invention in nonpolar media, such as n-alkanes or siloxanes, is substantially greater than that of the comparable hydroxyl-containing iodonium salts.

For example, the iodonium salt of the general formula (VII) has unrestricted solubility in toluol. In contrast, the comparable hydroxyl-containing iodonium salt of the general formula (VIII) is insoluble in toluol and shows no miscibility with organopolysiloxanes containing epoxy groups.

The invention additionally provides for a process for preparing the iodonium salts having reduced crystallization tendency. Iodonium salts of the invention are readily prepared by reaction with isocyanates.

"Photo"—OH + OCN—R⁴ → "Photo"—O—C(=O)—N(H)—R⁴ where "Photo" denotes a photoinitiator to be modified.

The process of the invention comprises reacting a hydroxyl-containing iodonium salt having the general formula (IX)

$$[R^1\text{—I—}R^2]^+X^- \quad \text{(IX)}$$

in which

I is iodine,

X⁻ is an anion of a complex metal salt and/or of a strong acid, $R^1$ is a radical $$\underset{F_c}{\overset{E_b}{-\text{Ar}-D'_a}}$$

which

Ar is an aromatic hydrocarbon radical, preferably, having 6 to 14 carbon atoms per radical or is an aromatic hydrocarbon radical containing at least one oxygen and/or sulfur atom and having 5 to 15 ring atoms per radical, a is 1, 2 or 3, b is 0, 1 or 2, c is 0, 1 or 2, D', E and F are each substituents of Ar, D' being a radical of the formula —(O)x—(R³)y—OH where x is 0 or 1, y is 0 or 1, $R^3$ is a linear or branched divalent hydrocarbon radical, preferably, having 1 to 40 carbon atoms per radical, which can be interrupted if desired by at least one oxygen atom and/or one sulfur atom and/or one carboxyl group, E is a radical of the formula

—O—R⁵,

F is a radical of the formula

—R⁶, $R^2$ is a radical of the formula $$\underset{F_e}{\overset{E_d}{-\text{Ar}}}$$

where $R^5$ is a monovalent hydrocarbon radical, preferably having 1 to 18 carbon atoms per radical, which can be interrupted if desired by at least one oxygen atom, $R^6$ is a monovalent hydrocarbon radical, preferably having 1 to 18 carbon atoms per radical, which can be interrupted if desired by at least one oxygen atom, d is 0, 1 or 2, and e is 0, 1 or 2, with a reagent containing isocyanate groups.

Preferred hydroxyl-containing iodonium salts are those of the general formula (X)

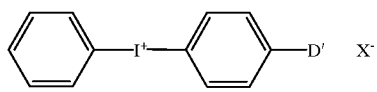 (X)

where D' and X⁻ are as defined previously.

Particularly preferred starting materials are iodonium salts of the formula (XI) below

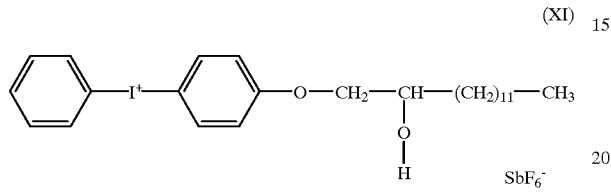 (XI)

Examples of reagents containing isocyanate groups, which may be reacted with hydroxyl-bearing iodonium salts, are those of the general formula (XII)

$$OCN-R^4 \quad (XII)$$

where $R^4$ is a monovalent linear, branched and/or cyclic alkyl, aryl, haloalkyl and/or haloaryl radical having 1 to 40 carbon atoms, which can, if desired, be interrupted by at least one oxygen atom and/or at least one sulfur atom and/or at least one urethane group and/or ester group, and which can, if desired, contain hydrophobicizing substituents and/or at least one isocyanate group.

Particularly preferred reagents containing isocyanate groups which may be reacted with hydroxyl-bearing iodonium salts are the following:

alkyl isocyanates, such as methyl, ethyl, propyl, butyl, sec-butyl, cyclohexyl, hexyl, octyl, tert-octyl, decyl, dodecyl and/or octadecyl isocyanate;

aryl isocyanates, such as phenyl, tolyl, dimethylphenyl, phenylethyl, propylphenyl, methoxyphenyl, (heptyloxy)phenyl, phenoxyphenyl, acetylphenyl, nitrophenyl, benzyl, methylbenzyl, methoxybenzyl, dimethyl-m-isopropenylbenzyl, naphthyl, (trifluoromethyl)phenyl, di(trifluoromethyl)phenyl, (trifluoromethylthio)phenyl and/or (trifluoromethoxy) phenyl isocyanate;

haloalkyl isocyanates, such as 2-bromomethyl isocyanate; haloaryl isocyanates, such as chlorobenzyl, chlorophenyl, trichlorophenyl, 4-bromo-2,6-dimethylphenyl, fluorophenyl, difluorophenyl, fluoro (trifluoromethyl)phenyl and/or fluorobenzyl isocyanate; diisocyanates, such as cyclohexane, dicyclohexylmethane 4,4'-, diphenylmethane 4,4'-, hexamethylene 1,6-, isophorone, and/or tolylene diisocyanate;

polymeric isocyanates, such as Desmodur N 3300 from Bayer AG, Desmodur L from Bayer AG, Desmodur E41 from Bayer AG, Desmodur Z 4370 from Bayer AG;

polydimethylsiloxane isocyanates, such as

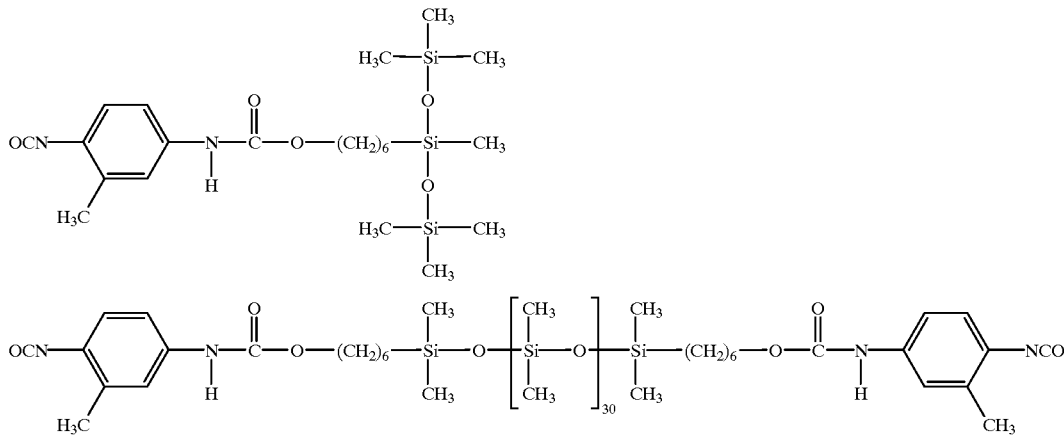

The iodonium salts of the invention are suitable, for example, as photoinitiators for the polymerization of cationically polymerizable organic substances, such as epoxides, vinyl ethers, organopolysiloxanes containing epoxy groups, organopolysiloxanes containing alkenyloxy groups, such as vinyloxy groups or propenyloxy groups, and olefins. Such substances are described, for example, in U.S. Pat. No. 5,057,549, DE-A-40 02 922, and in the patent documents cited at the outset.

WORKING EXAMPLES

Example 1

10 g of a commercial photoinitiator of the formula (XI) were suspended in 10 ml of ethyl acetate, mixed with 1.0 g of ethyl isocyanate and two drops of COSMOS® 29* as catalyst, and heated at 60° C. in a waterbath. The mixture was stirred for 2 h. After the reaction, the solvent was removed by distillation. This left a yellow, viscous product.
*Commercial product of Goldschmidt AG

Example 2

10 g of a commercial photoinitiator of the formula (XI) were suspended in 10 ml of ethyl acetate, mixed with 1.7 g of hexyl isocyanate and two drops of COSMOS® 29 as catalyst, and heated at 60° C. in a waterbath. The mixture was stirred for 2 h. After the reaction, the solvent was removed by distillation. This left a yellow, viscous product.

Example 3

10 g of a commercial photoinitiator of the formula (XI) was suspended in 10 ml of ethyl acetate, mixed with 1.6 g of phenyl isocyanate and two drops of COSMOS® 29 as catalyst, and heated at 60° C. in a waterbath. The mixture was stirred for 2 h. After the reaction, the solvent was removed by distillation. This left a yellow, viscous product.

Example 4

10 g of a commercial photoinitiator of the formula (XI) was suspended in 10 ml of ethyl acetate, mixed with 2.5 g of m-(trifluoromethyl)phenyl isocyanate and two drops of COSMOS® 29 as catalyst, and heated at 60° C. in a waterbath. The mixture was stirred for 2 h. After the reaction, the solvent was removed by distillation. This left a yellow, viscous product.

Comparison 1

The solubility of the iodonium salts of the invention was compared with the solubility of the hydroxyl-bearing iodonium salts. The results are summarized in Table 1:

TABLE 1

| Photoinitiator | Solubility in toluene |
| --- | --- |
| Formula (XI) | insoluble |
| Ex. 1 | soluble to a clear solution |
| Ex. 2 | soluble to a clear solution |

TABLE 1-continued

| Photoinitiator | Solubility in toluene |
| --- | --- |
| Ex. 3 | soluble to a clear solution |
| Ex. 4 | soluble to a clear solution |

The solubility difference between the hydroxyl-containing photoinitiator with the formula (XI) and the photoinitiators of the invention, containing urethane groups and intended for cationic curing, is considerable.

Comparison 2

The reduction in the crystallization tendency may be demonstrated with particular clarity on the basis of the melting point of the compounds.

TABLE 2

| Photoinitiator | Melting point |
| --- | --- |
| Formula (XI) | 91° C. |
| Ex. 1 | viscous oil |
| Ex. 2 | viscous oil |
| Ex. 3 | viscous oil |
| Ex. 4 | viscous oil |

It is found that by means of the modification the melting point and thus the crystallization tendency were reduced considerably.

Comparison 3

The improved hydrolytic stability of the iodonium salts of the invention containing urethane groups may best be shown in comparison with the iodonium salt with the formula (XVI), containing Si—O—C bonds (see German Patent Application 19901531.7).

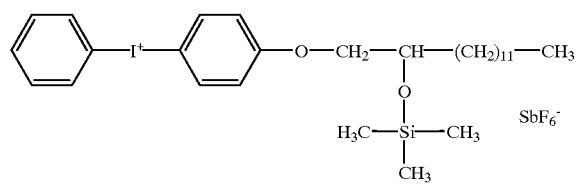

(XVI)

The results are summarized in Table 3. Indicated is the time to the formation of visible precipitates or crystals of the hydrolytic cleavage product with the formula (XI):

| Photoinitiator | Stability in toluene (50% w/w) | Stability in 1-butanol (50% w/w) |
| --- | --- | --- |
| Formula (XVI) | 21 d | 2 d |
| Ex. 1 | >90 d | >90 d |
| Ex. 2 | >90 d | >90 d |
| Ex. 3 | >90 d | >90 d |
| Ex. 4 | >90 d | >90 d |

Tests Relating to Cationic Photopolymerization

In order to examine the activity of the compounds shown in Examples 1–4 in cationic photopolymerization, 98 parts of a cycloaliphatic epoxysilane having an epoxy value of 3.5% and a viscosity of 125 mPas were mixed with 2 parts of each photoinitiator.

The mixtures were then applied to a standard OPP film (30 μm) using a pilot-scale coating machine equipped with a five-roll applicator unit. The application weight was 0.5–1 g/m². The coatings were subsequently cured with a microwave-excited UV lamp (Fusion, 120 W/cm) at a web speed of 20 m/min.

Directly following passage under the UV lamp, it was determined whether the coatings have cured to a film which is no longer tacky.

The results are summarized in the table below:

| Photoinitiator | Appearance of the mixture | Curing after the UV lamp |
|---|---|---|
| Formula (VIII) | cloudy, crystalline precipitate | unsatisfactory; cloudy, tacky film; crystals visible |
| Ex. 1 | opaque | curing; film no longer tacky |
| Ex. 2 | clear | good curing; clear film, no longer tacky |
| Ex. 3 | clear | good curing; clear film, no longer tacky |
| Ex. 4 | clear | good curing; clear film, no longer tacky |

It was found that the differences in curing behavior between the hydroxyl-containing photoinitiator with the formula (VIII) and the photoinitiators of the invention containing urethane groups are considerable.

The above description of the invention is intended to be illustrative and not limiting. Various changes in the embodiments may occur to those skilled in the art. These changes can be made without departing from the scope of the invention.

What is claimed is:

1. An iodonium salt of the formula (IV)

$$[R^1\text{—I—}R^2]^+X^- \quad (IV)$$

where

I is iodine, $X^-$ is an anion of a complex metal salt and/or of a strong acid, $R^1$ is the radical

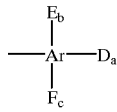

in which

Ar is an aromatic hydrocarbon or is an aromatic hydrocarbon radical containing at least one oxygen and/or sulfur atom, a is 1, 2 or 3, b is 0, 1 or 2, c is 0, 1 or 2, D, E and F are each substituents of Ar, D being a radical of the formula

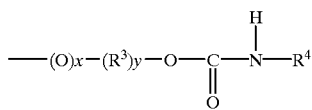

where x is 0 or 1, y is 0 or 1, $R^3$ is a linear or branched divalent hydrocarbon radical which is optionally interrupted by at least one oxygen atom, one sulfur atom, and/or one carboxyl group, $R^4$ is a monovalent linear, branched and/or cyclic alkyl, linear, branched and/or cyclic haloalkyl, aryl and/or haloaryl radical, which is optionally interrupted by at least one oxygen atom, at least one sulfur atom, at least one urethane group and/or at least one ester group, and which optionally contains hydrophobicizing substituents and/or at least one isocyanate group, E is a radical of the formula $$\text{—O—}R^5$$

F is a radical of the formula $$\text{—}R^6$$

$R^2$ is a radical of the formula

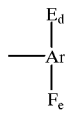

where $R^5$ is a monovalent hydrocarbon radical, which is optionally interrupted by at least one oxygen atom, $R^6$ is a monovalent hydrocarbon radical, which is optionally interrupted by at least one oxygen atom, d is 0, 1 or 2, and e is 0, 1 or 2.

2. An iodonium salt as claimed in claim 1, wherein

I is iodine, $X^-$ is an anion of a complex metal salt and/or of a strong acid, $R^1$ is the radical

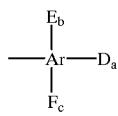

in which

Ar is an aromatic hydrocarbon radical having 6 to 14 carbon atoms per radical or is an aromatic hydrocarbon radical containing at least one oxygen and/or sulfur atom and having 5 to 15 ring atoms per radical a is 1, 2 or 3, b is 0, 1 or 2, c is 0, 1 or 2, D, E and F are each substituents of Ar,
D being a radical of the formula

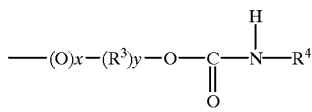

where
x is 0 or 1,
y is 0 or 1,
$R^3$ is a linear or branched divalent hydrocarbon radical having 1 to 40 carbon atoms per radical which is optionally interrupted by at least one oxygen atom, one sulfur atom, and/or one carboxyl group,
$R^4$ is a monovalent linear, branched and/or cyclic alkyl, linear, branched and/or cyclic, haloalkyl, aryl and/or haloaryl radical having 1 to 40 carbon atoms, which is optionally interrupted by at least one oxygen atom, at least one sulfur atom, at least one urethane group and/or ester group, and which optionally contains hydrophobicizing substituents and/or at least one isocyanate group,
E is a radical of the formula

F is a radical of the formula

$R^2$ is a radical of the formula

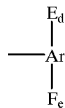

where
$R^5$ is a monovalent hydrocarbon radical 1 to 18 carbon atoms per radical, which is optionally interrupted by at least one oxygen atom,
$R^6$ is a monovalent hydrocarbon radical 1 to 18 carbon atom per radical, which is optionally interrupted by at least one oxygen atom,
d is 0, 1 or 2, and
e is 0, 1 or 2.

3. An iodonium salt as claimed in claim 1, wherein at least one of the radicals $R^4$, $R^5$ and $R^6$ is an alkyl radical.

4. The iodonium salt as claimed in claim 3, wherein the alkyl radical is methyl, ethyl, n-propyl, isopropyl, n-butyl, isobutyl, tert-butyl, n-pentyl, isopentyl, neopentyl, tert-pentyl radical, n-hexyl, cyclohexyl, n-heptyl, n-octyl, 2,2,4-trimethylpentyl, n-nonyl, n-decyl, n-dodecyl or n-octadecyl radical.

5. An iodonium salt as claim in claimed 1, wherein at least one of the radicals $R^4$, $R^5$, and $R^6$ is an aryl radical.

6. An iodonium salt as claimed in claim 5, wherein the aryl radical is phenyl, naphthyl or anthryl.

7. An iodonium salt as claimed in claim 1, wherein at least one of the radicals $R^4$, $R^5$, and $R^6$ is a haloalkyl radical.

8. An iodonium salt as claimed in claim 7 wherein the haloalkyl radical is chloromethyl, trichloromethyl, trifluoromethyl, pentafluoroethyl or heptafluoropropyl.

9. An iodonium salt as claimed in claim 1, wherein at least one of the radicals $R^4$, $R^5$, and $R^6$ is a haloaryl radical.

10. An iodonium salt as claimed in claim 9, where the haloaryl radical is bromophenyl, chlorophenyl, fluorophenyl, difluorophenyl, fluoro(trifluoromethyl)phenyl, pentafluorophenyl, (trifluoromethyl)phenyl, trifluoromethylthio)phenyl or (trifluoromethoxy)phenyl radical.

11. An iodonium salt as claimed in claim 1, wherein at least one of the radicals $R^4$, $R^5$, and $R^6$ is a hydrocarbon radical, interrupted by at least one oxygen atom and/or sulfur atom.

12. An iodonium salt as claimed in claim 11, where the radical is $-CH_2-CH_2-O-CH_3$, $-CH_2-CH_2O-CH_2CH_3$ or $-CH_2-CH_2-S-CH_2CH_3$.

13. An iodonium salt as claimed in claim 1, wherein X is selected independently from the group consisting of tosylate, $SbF_6^-$, $PF_6^-$, $BF_4^-$, $F_3CSO_3^-$, $F_3CCO_2^-$, $AsF_6^-$, $ClO_4^-$, and $HSO_4^-$.

14. An iodonium salt as claimed in claim 1 with the formula (V)

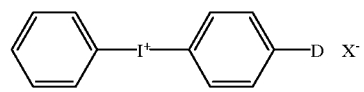

wherein D and $X^-$ are as already defined.

15. An iodonium salt as claimed in claim 1 wherein
D is

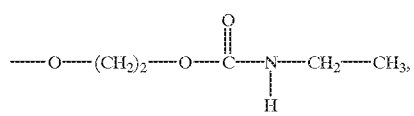

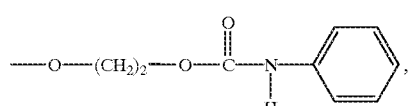

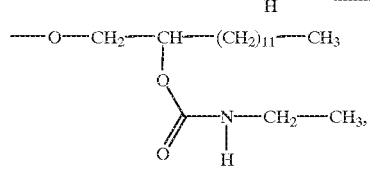

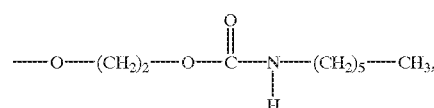

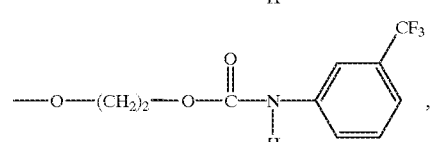

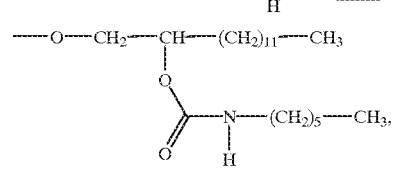

-continued
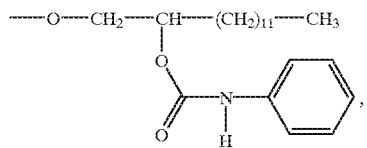
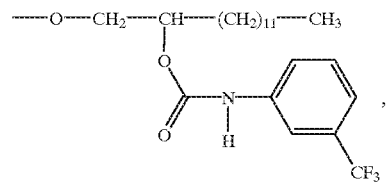
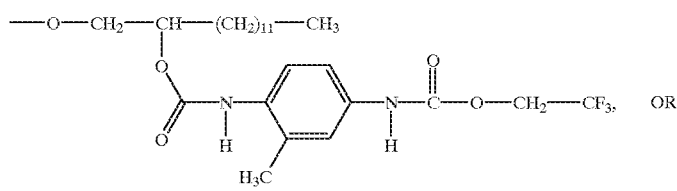
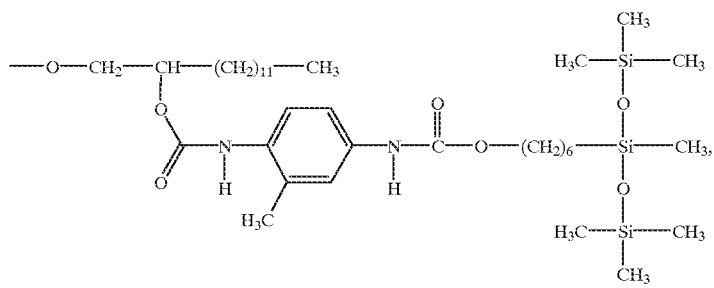
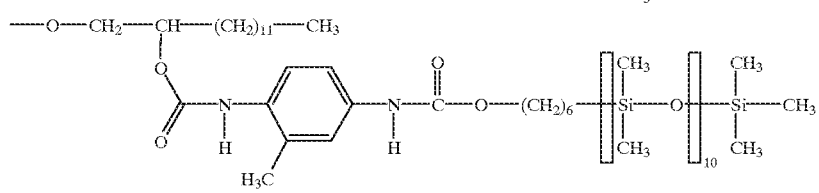  OR
E is methoxy, ethoxy or n-butoxy
F is methyl, ethyl, propyl, 2-methylpropyl and n-butyl.
16. An iodonium salt as claimed in claim 1 wherein $R^1$ is
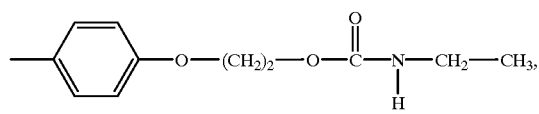
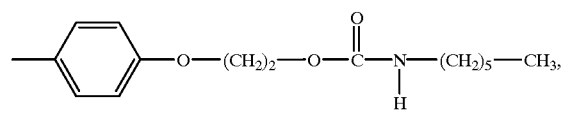
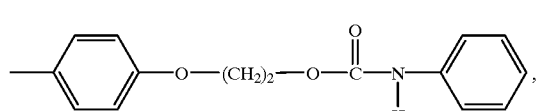
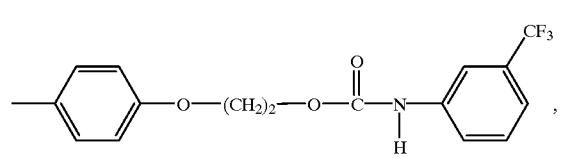
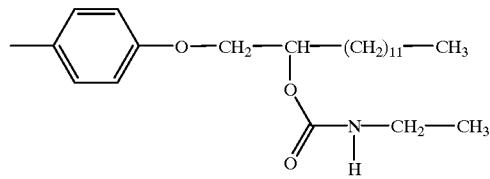
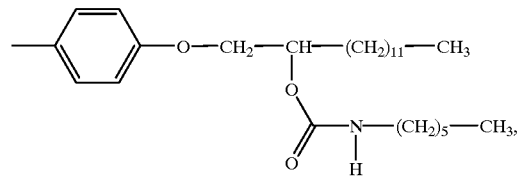
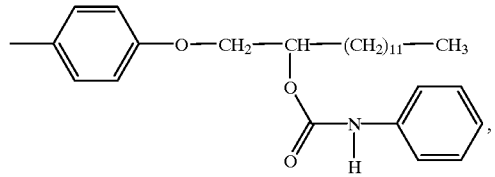
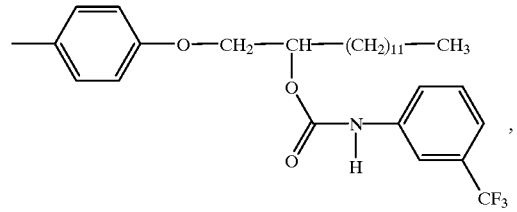

-continued

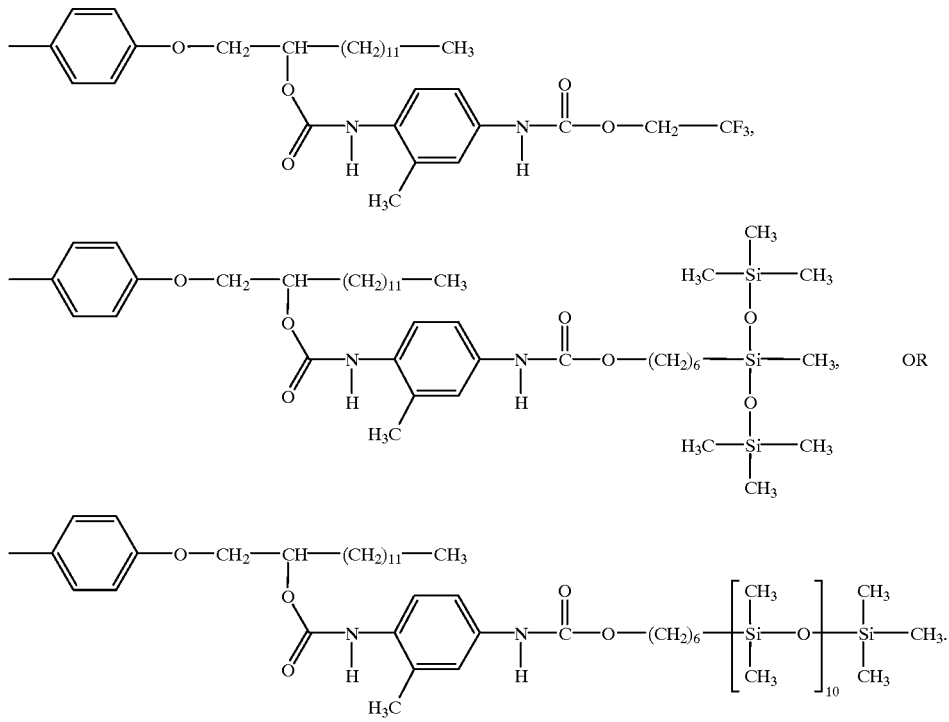

17. A process for preparing the iodonium salt as claimed in claim 1, which comprises reacting a hydroxyl-containing iodonium salt having the formula $$[R^1\text{—}I\text{—}R^2]^+X^- \quad (IX)$$

in which
I is iodine,
$X^-$ is an anion of a complex metal salt and/or of a strong acid,
$R^1$ is a radical

in which
Ar is an aromatic hydrocarbon radical having or is an aromatic hydrocarbon radical containing at least one oxygen and/or sulfur atom
a is 1, 2 or 3,
b is 0, 1 or 2,
c is 0, 1 or 2,
D', E and F are each substituents of Ar,
D' being a radical of the formula

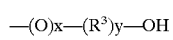

where
x is 0 or 1,
y is 0 or 1,
$R^3$ is a linear or branched divalent hydrocarbon radical which is optionally interrupted by at least one oxygen atom, one sulfur atom, one carboxyl group, E is a radical of the formula

F is a radical of the formula

$R^2$ is a radical of the formula

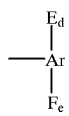

where
$R^5$ is a monovalent hydrocarbon radical, which is optionally interrupted by at least one oxygen atom,
$R^6$ is a monovalent hydrocarbon radical, which is optionally interrupted by at least one oxygen atom,
d is 0, 1 or 2, and
e is 0, 1 or 2,
with a reagent containing isocyanate groups.

18. The process as claimed in claim 17, wherein hydroxyl-containing iodonium salts used are those of the formula (X)

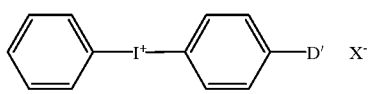

(X)

wherein D' and $X^-$ are as defined.

19. The process as claimed in claim 17, wherein hydroxyl-containing iodonium salts used are those of the formula (XI):

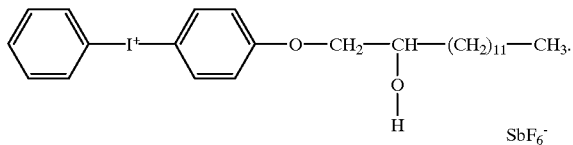 (XI)

20. A process as claimed in claim 17, wherein reagents containing isocyanate groups, of the general formula (XII)

OCN—R$^4$ (XII), are reacted, where

R$^4$ is a monovalent linear, branched and/or cyclic alkyl, aryl, linear, branched and/or cyclic haloalkyl and/or haloaryl radical which is optionally interrupted by at least one oxygen atom, at least one sulfur atom, at least one urethane group and/or ester group, and which is optionally contains hydrophobicizing substituents and/or at least one isocyanate group.

21. A method for polymerizing cationic polymerizable organic monomers which comprises adding a photoinitiator comprising a compound according to claim 1 and cationically polymerizing the monomer.

22. The method as claimed in claim 21 wherein the monomers are epoxides, vinyl ethers, organopolysiloxanes containing epoxy groups, organopolysiloxanes containing alkenyloxy groups, and/or olefins.

* * * * *